(12) United States Patent
Boiten

(10) Patent No.: US 11,911,296 B2
(45) Date of Patent: Feb. 27, 2024

(54) ORTHOPEDIC JOINT

(71) Applicant: Ottobock SE & Co. KGaA, Duderstadt (DE)

(72) Inventor: Herman Boiten, Ede (NL)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

(21) Appl. No.: 16/755,869

(22) PCT Filed: Oct. 8, 2018

(86) PCT No.: PCT/EP2018/077317
§ 371 (c)(1),
(2) Date: Apr. 13, 2020

(87) PCT Pub. No.: WO2019/076664
PCT Pub. Date: Apr. 25, 2019

(65) Prior Publication Data
US 2021/0196483 A1 Jul. 1, 2021

(30) Foreign Application Priority Data

Oct. 18, 2017 (DE) .................. 10 2017 124 337.2

(51) Int. Cl.
*A61F 2/64* (2006.01)
*A61F 2/50* (2006.01)
(Continued)

(52) U.S. Cl.
CPC ................. *A61F 2/64* (2013.01); *A61F 2/68* (2013.01); *A61F 5/0123* (2013.01); *F15B 15/12* (2013.01);
(Continued)

(58) Field of Classification Search
CPC ............................................ A61F 2002/5006
See application file for complete search history.

(56) References Cited

U.S. PATENT DOCUMENTS

| | | | | |
|---|---|---|---|---|
| 2,701,372 A | * | 2/1955 | Tisdale | A61F 2/64 623/44 |
| 5,704,945 A | * | 1/1998 | Wagner | A61F 2/64 623/44 |

(Continued)

FOREIGN PATENT DOCUMENTS

| | | |
|---|---|---|
| CN | 1141157 A | 1/1997 |
| CN | 1972649 A | 5/2007 |

(Continued)

OTHER PUBLICATIONS

"International Search Report and Written Opinion of the International Searching Authority," issued in connection with Int'l Appl. No. PCT/EP2018/077317, dated Feb. 12, 2019 (16 pages).

(Continued)

*Primary Examiner* — Jacqueline Woznicki
(74) *Attorney, Agent, or Firm* — HOLLAND & HART LLP

(57) ABSTRACT

An orthopedic joint for a prosthesis, includes an upper part, a lower part which is mounted on the upper part in a pivotal manner about a pivot axis, and a rotation hydraulic unit, which has a housing with a chamber and a pivot piston that is pivotally mounted in the chamber and divides the chamber into a flexion chamber and an extension chamber, the chambers being hydraulically connected together via at least one channel. The joint also includes a pretensioning device which supports a pivoting movement of the upper part relative to the lower part, wherein the pretensioning device is coupled directly to the pivot piston via a support.

18 Claims, 4 Drawing Sheets

(51) Int. Cl.
  *A61F 2/74* (2006.01)
  *A61F 2/68* (2006.01)
  *A61F 5/01* (2006.01)
  *F15B 15/12* (2006.01)

(52) U.S. Cl.
  CPC .............. *A61F 2/74* (2021.08); *A61F 2/744* (2021.08); *A61F 2002/5006* (2013.01); *A61F 2002/5073* (2013.01); *A61F 2002/5087* (2013.01)

(56) References Cited

U.S. PATENT DOCUMENTS

| | | | |
|---|---|---|---|
| 5,755,813 A | 5/1998 | Krukenberg | |
| 5,888,212 A * | 3/1999 | Petrofsky | A61F 2/70 623/24 |
| 6,113,642 A * | 9/2000 | Petrofsky | F16F 9/46 623/24 |
| 7,066,964 B2 | 6/2006 | Wild | |
| 7,278,522 B2 | 10/2007 | Reinhardt et al. | |
| 8,814,949 B2 * | 8/2014 | Gramnaes | A61F 2/64 623/27 |
| 8,915,969 B2 * | 12/2014 | Boender | A61F 2/68 623/26 |
| 9,066,819 B2 | 6/2015 | Gramnaes | |
| 9,913,738 B1 | 3/2018 | Fikes | |
| 10,231,850 B2 * | 3/2019 | Shen | A61F 2/64 |
| 2004/0186591 A1 * | 9/2004 | Lang | A61F 2/64 623/44 |
| 2005/0203639 A1 * | 9/2005 | Wild | A61F 2/68 623/44 |
| 2005/0258009 A1 * | 11/2005 | Reinhardt | F16F 9/535 188/266.5 |
| 2006/0293761 A1 * | 12/2006 | Baumann | A61F 2/64 623/44 |
| 2007/0173953 A1 * | 7/2007 | Imakita | A61F 2/68 251/14 |
| 2007/0208430 A1 | 9/2007 | Gramnäs | |
| 2008/0255670 A1 * | 10/2008 | Boiten | A61F 2/60 623/18.11 |
| 2008/0281427 A1 * | 11/2008 | Shen | A61F 2/64 623/20.29 |
| 2014/0074255 A1 * | 3/2014 | Starker | A61F 2/68 623/50 |
| 2014/0277581 A1 * | 9/2014 | Steele | A61F 2/64 623/24 |
| 2018/0177615 A1 * | 6/2018 | Cheng | A61F 2/68 |

FOREIGN PATENT DOCUMENTS

| | | |
|---|---|---|
| DE | 195 06 426 C1 | 11/1996 |
| DE | 297 23 632 U1 | 1/1999 |
| DE | 20 2004 008 024 U1 | 11/2005 |
| DE | 10 2005 029160 A1 | 12/2006 |
| EP | 1 736 121 B1 | 7/2008 |
| WO | 1999000075 A1 | 1/1999 |

OTHER PUBLICATIONS

Chinese Patent Office, "Office Action and Search Report", issued in connection with Chinese Patent Application No. 201880067396.8 dated Sep. 1, 2022 (17 pages) (11 pages of English Translation and 6 pages of Original Document).

* cited by examiner

ORTHOPEDIC JOINT

CROSS REFERENCE TO RELATED APPLICATIONS

This application is a U.S. National Entry and claims priority to PCT International Patent Application No. PCT/EP2018/077317, filed 8 Oct. 2018, and entitled "ORTHOPEDIC JOINT", which claims priority to Germany Patent Application No. 10 2017 124 337.2 filed 18 Oct. 2017, the entire disclosures of which are incorporated herein by this reference.

TECHNICAL FIELD

The invention relates to an orthopedic joint, comprising an upper part, a lower part mounted on the upper part so as to pivot about a pivot axis, and a rotation hydraulics unit, which has a pivot housing with a chamber and with a pivot piston which is mounted pivotably in the latter and divides the chamber into a flexion chamber and an extension chamber, said chambers being connected hydraulically to each other via at least one channel, and with a pretensioning device which assists a pivoting movement of the upper part relative to the lower part.

BACKGROUND

Orthopedic joints for orthopedic devices such as orthoses or exoprostheses serve to connect an upper part to a lower part in an articulated manner. Between the upper part and the lower part, a pivot axis is formed which, in the case of a monocentric joint, has a fixed relationship to the upper part and to the lower part, whereas, in the case of a polycentric joint, the pivot axis can change relative to the upper part or the lower part over the pivot angle.

DE 297 23 632 UI discloses a computer-controlled hydraulic resistance device for a prosthesis with a prosthesis socket for an upper leg stump, a knee control arrangement with a resistance device, a lower leg tube, and a prosthetic foot. An upper part in the form of a knee bracket has a rotor shaft on which a wing is arranged. By way of the rotor shaft, the knee bracket can be moved together with the wing relative to a frame which forms the lower part and which has a recess for a lower leg tube. A housing in which the wing is pivoted is formed inside the frame, such that a rotation hydraulics unit forms. By way of a connection channel in which throttles and valves are arranged, the hydraulic fluid is conveyed from an extension chamber into a flexion chamber, and vice versa, during the rotation. In the fluid stream, a chamber is arranged in which a piston and a spring are arranged, ensuring a complete extension of the prosthetic knee joint.

EP 1 736 121 B1 relates to a hydraulic knee-joint prosthesis with a joint unit, a foot attachment unit, and a tube connecting the two components, the joint unit having a rotation axis with a damper chamber and a damper wing movable therein, activated by a hydraulic control. The foot attachment unit is connected to a central valve unit via a control line. By way of pressure points in the foot attachment unit, a pressure chamber acts on the control line so as to activate the central valve unit. To ensure that extension can be easily performed after the flexion of the knee joint, the extension chamber is connected by a further hydraulic line to a hydraulic spring store which is subjected to the circulating oil from the damper chamber, in order to again release the energy, stored in the flexion, for the reversal of movement. The spring store acts on a piston, which applies pressure to the hydraulic fluid.

U.S. Pat. No. 7,066,964 B2 relates to a prosthetic knee joint with rotation hydraulics. In a housing in an upper part, a rotary piston is pivoted via a front link of a polycentric knee joint. Extension assistance is achieved via a spring-loaded lever mechanism which acts on a rear link.

DE 195 06 426 C1 relates to a brake-action knee joint for a leg prosthesis, comprising a joint upper part, a joint lower part, a joint pin connected to a joint part for conjoint rotation therewith, and a rocker which forms a joint middle part and which has its extension-side end fixed to a rocker pin lying parallel, ventrally and distally with respect to the joint pin and has its flexion-side end surrounding the joint pin. A brake device is controlled via a foot load. Inside the brake-action knee joint, a rotation hydraulics unit is arranged in which an oil line can be completely or partially closed by a valve plunger. A connecting rod which acts as an extension assist is articulated with one end to the joint upper part and is articulated with the other end to a spring clamp which is arranged in the joint lower part and is acted upon by an extension assist spring.

A problem with the devices of the prior art is that the extension assists require intensive maintenance, can catch on items of clothing and, if dirtied, tend to become worn and possibly generate noise.

SUMMARY

The object of the present invention is to make available a construction which is simplified in relation to the prior art and in which wear is minimized and safe handling ensured.

According to the invention, this object is achieved by an orthopedic joint having the features disclosed herein. Advantageous embodiments and developments of the invention are disclosed in the description and the figures.

In the orthopedic joint according to the invention, e.g. for prostheses or orthoses, comprising an upper part, a lower part mounted on the upper part so as to pivot about a pivot axis, and a rotation hydraulics unit, which has a housing with a chamber and with a pivot piston which is mounted pivotably in the latter and divides the chamber into a flexion chamber and an extension chamber, said chambers being connected hydraulically to each other via at least one channel, and with a pretensioning device which assists a pivoting movement of the upper part relative to the lower part, provision is made that the pretensioning device is coupled directly to the pivot piston via a support. By virtue of the direct coupling of the support to the pivot piston, the assistance force, in particular for assisting an extension movement or an extension, is exerted directly on the pivot piston, which is in turn connected to the upper part or the lower part for conjoint rotation therewith. By virtue of the force applied to the pivot piston, the pivoting movement intended in each case is assisted. The arrangement of the support as a mechanical solid-body component at the pivot piston has the effect that at least a part of the support is guided inside the hydraulic fluid, as a result of which contact of the pretensioning device with the air is avoided. The support, via which the pretensioning force is transmitted to the pivot piston, is located inside the wet region of the hydraulics, such that there is no need for an extension assist located outside the rotation hydraulics or for a force transmission element arranged outside the hydraulics. By virtue of the guiding inside the hydraulics, noise development is avoided or at least attenuated. Wear is minimized by the fact that the pretensioning or extension assist device is arranged inside the hydraulic fluid, which is generally a hydraulic oil, since the hydraulic fluid at the same time shields against contact with water and additionally ensures lubrication.

In a development of the invention, provision is made that the support is mounted pivotably in or at the pivot piston, as a result of which it is possible to ensure that a very high flexion angle of the upper part relative to the lower part can be achieved about the pivot axis. For the transmission of compressive forces, it is advantageous if the support is stable against buckling, in which case the support cannot just transmit compressive forces from the pretensioning device to the pivot piston but, in a variant of the invention, can also take up tensile forces. Depending on the design of the pretensioning device, it is also possible that only tensile forces are transmitted to the pivot piston via the support, if the pretensioning device has a tension spring.

The support is preferably guided completely in the hydraulic fluid, as a result of which the installation space made available by the joint is utilized optimally. The pretensioning device can have a spring, on or at which the support is mounted. The spring is in particular designed as a helical spring or coil spring, which can likewise be mounted in the hydraulic fluid. By the arrangement of a slide piece, it is possible to achieve an optimized bearing of the support on the spring, such that the spring properties can be set independently of the bearing properties. Thus, for example, a coil spring or helical spring can be used, in the end of which the slide piece is fitted, on which slide piece the support in turn can then be mounted to transmit forces, in particular can be mounted to transmit compressive force. It is likewise possible that the spring is designed as an elastomer element or also as an encapsulated air cushion on which the slide piece provides an improved pressure distribution. In the case of an elastomer element or a pressure cushion, the hydraulic structure is configured such that the hydraulic liquid or the oil can be displaced, for example into a compensation container, such that, inside the chambers, there is no build-up of pressure in the fluid caused by the pretensioning device.

In a variant of the invention, provision is made that the slide piece is guided in a bushing, in particular in a rectilinear bushing. The bushing can be screwed into the housing or into the upper part or lower part or can be inserted or secured therein in another way. The bushing is connected fluidically to the chamber and thus constitutes a part of the hydraulic system. Thus, both the spring of the pretensioning device and also the slide piece and the support are located inside the hydraulic fluid, such that all of the moved components of the pretensioning device and of the device for assisting the pivoting movement are mounted inside the hydraulic fluid. In this way, the wear of the slide piece too and the noise development are reduced overall. In addition, the direct connection of the pretensioning device and of the support to the pivot piston means that the number of structural parts can be kept to a minimum. There is no need for separate bearing points requiring separate lubrication or a complicated slide bearing.

At least one recess and/or a passage for the hydraulic fluid can be arranged or formed in the slide piece, such that the hydraulic fluid can pass from the chamber, in which the pivot piston is located, into a space into and out of which the slide piece is moved if the pivot piston is moved. The at least one recess and/or damping is of such dimension that no appreciable damping is generated. The damping generated by the flow resistance of the slide piece is undesirable in principle, since it works against the pivoting movement of the rotation piston in a way that cannot be influenced. The configuration of the slide piece is preferably such that a minimum, negligible damping is generated.

The pretensioning device is preferably designed such that no appreciable forces are transmitted by it to the fluid, and instead the pretensioning device acts on the pivot piston only, or almost exclusively, via the support. In this way, hydraulic effects and influences of the pivoting movement are separated from each other by the pretensioning device, such that no interactions have to be taken into consideration in the adjusting of the joint.

A recess in which the support is received can be formed in the pivot piston. By virtue of the recess inside the pivot piston, the pivoting angle can be further increased since, in a pivoting movement to an extreme position, the support can engage in the contour of the pivot piston, wherein the recess is not of a continuous form, such that the pivot piston still separates the extension chamber from the flexion chamber.

The support can have an S-shaped contour in order to allow the end positions of the pivot piston to lie as far apart as possible from each other, so as to permit a maximum flexion of the joint. By virtue of the design of the pivot piston with a recess, and by virtue of the S-shaped contour of the support, flexion angles of more than 150° can be achieved.

In a variant of the invention, provision is made that the coupling point of the pivot piston to the support lies on different sides of the pivot axes in the end positions of the pivot piston, as a result of which it is also possible, among other things, to ensure that, with a pretensioning of the support by the pretensioning device to one of the end positions, the respective end position is secured, such that, for example, an increased force has to be applied in order to get to the extension from a position of maximum flexion or to the flexion from a position of maximum extension.

To permit a volume transport from the extension chamber into the flexion chamber and vice versa, a channel is arranged between the chambers, through which channel hydraulic fluid can flow when the pivot piston is moved. The channel is preferably formed in that housing in which the chamber, with the pivot piston mounted therein, is also formed. The channel can also be configured separately as a conduit. A preferably adjustable throttle can be arranged in the channel, with which throttle the pivoting resistance of the joint device can be modified on account of an adjustable hydraulic resistance. The throttle can provide a permanent resistance, and it is likewise possible, with a suitable hydraulic set-up, to provide different resistances in the extension direction and the flexion direction. Likewise, with a bypass valve, the pivoting movement in one direction can be executed almost without hydraulic resistance. It is likewise possible, via a sensor device and a control device and an adjustment device, to couple a computer-controlled knee joint to the pretensioning device, as described above.

The orthopedic joint is suitable in particular for a prosthesis or orthosis, is in particular designed as a prosthetic joint or orthotic joint, and, in one embodiment of the invention, is designed as a prosthetic knee joint.

BRIEF DESCRIPTION OF THE DRAWINGS

An illustrative embodiment of the invention is explained in more detail below with reference to the attached figures, in which.

DETAILED DESCRIPTION

Figure 1:
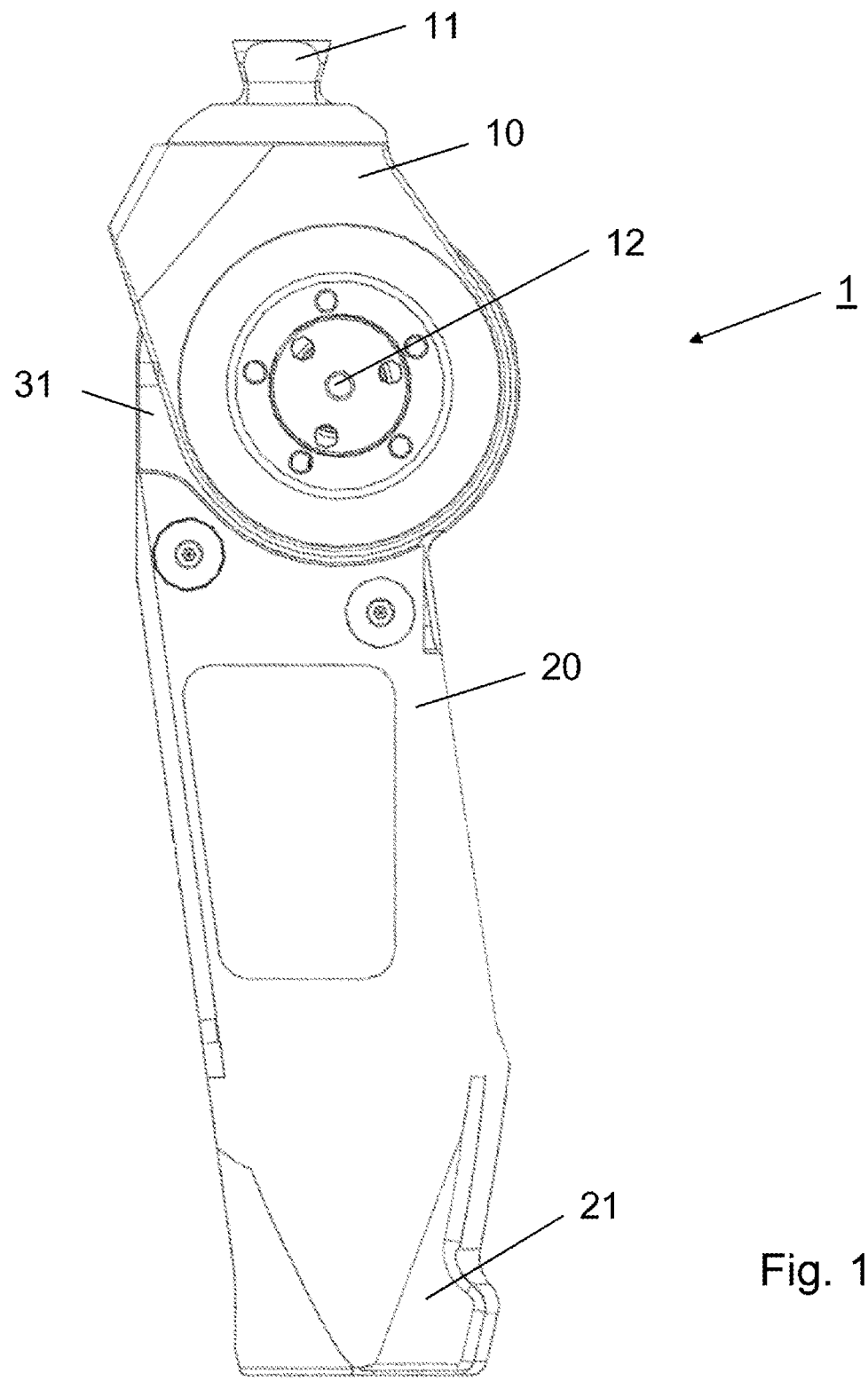
FIG. 1 shows a side view of an artificial joint in the form of a prosthetic knee joint.

FIG. 1 shows a side view of an orthopedic joint in the form of an exoprosthetic knee joint 1 which has an upper part 10 with upper connection means 11 in the form of a pyramid adapter. A prosthesis socket for receiving an upper leg stump can be secured at the upper connection means 11. The upper part 10 is mounted so as to be pivotable about a pivot axis 12 about a lower part 20, at the distal end of which a receptacle 21 for a lower leg tube is formed. A housing 30 in which a rotation hydraulics unit is accommodated, is formed or arranged inside the lower part 20. Further components of the rotation hydraulics unit can be arranged inside the lower part 20, as is explained in connection with FIG. 2.

Figure 2:
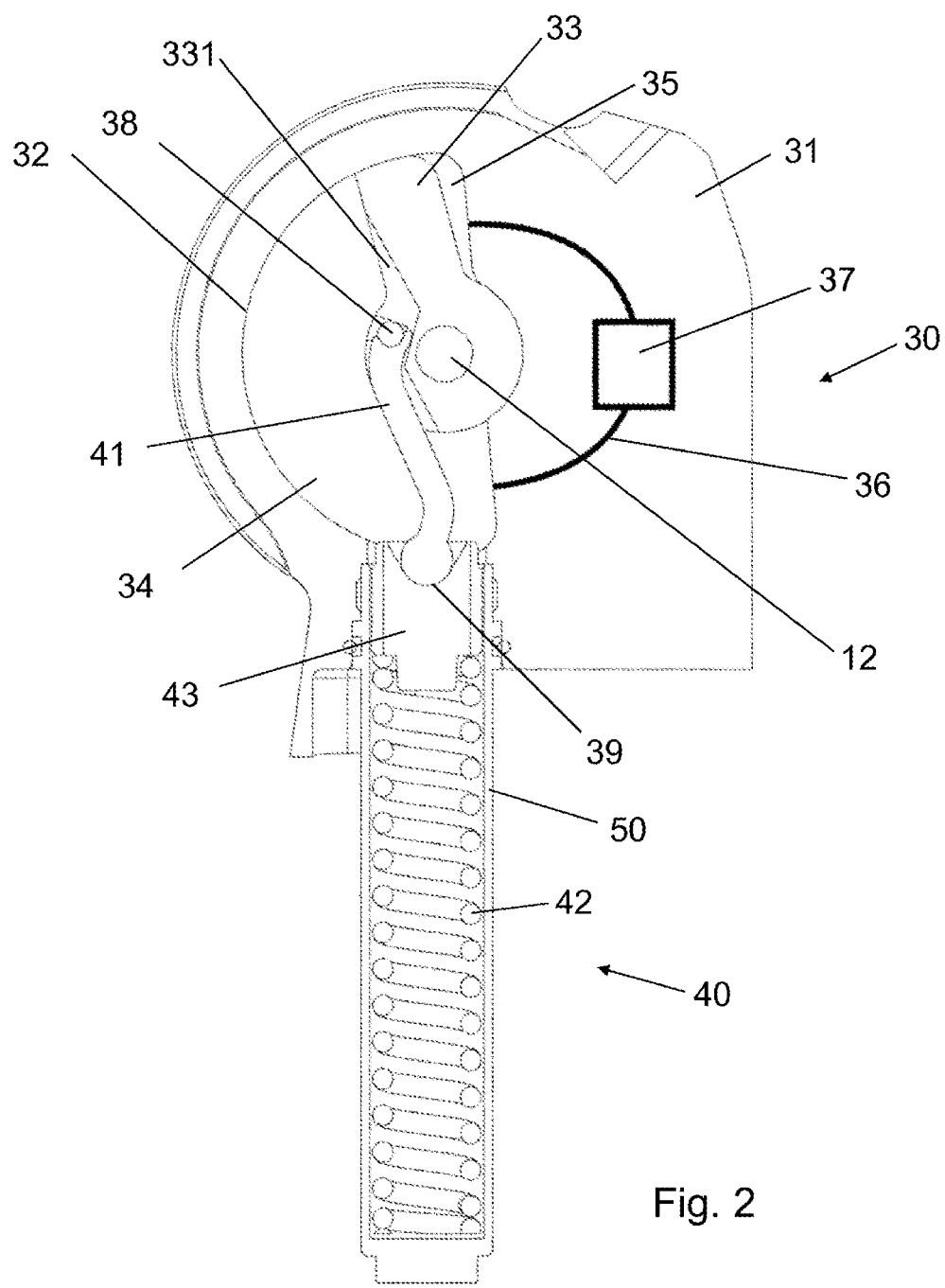
FIG. 2 shows a partial sectional view of the prosthetic knee joint according to FIG. 1.

FIG. 2 shows a sectional view of a part of the prosthetic knee joint 1 according to FIG. 1 with a housing 30 in which a chamber 32 is formed in which a pivot piston 33 is mounted pivotably about the pivot axis 12. The prosthetic knee joint 1 is designed as a monocentric knee joint, and the pivot piston 33 is connected to the upper part 10 for conjoint rotation with the latter. In the position shown in FIG. 2, the pivot piston 33 is located in the extension end position, in which the prosthetic knee joint has reached a maximum extension. In the illustrative embodiment shown, an extension stop is provided by external bumpers in the upper part, and the forces occurring in the extreme position are transmitted to the hydraulics part. The end stop in the joint is not formed via the pivot piston 33, among other reasons so that the latter does not have to be designed for the high mechanical forces that may occur in an end stop. The pivot piston 33 divides the chamber 20 into an extension chamber 35 and a flexion chamber 34. If the upper part 10 is pivoted relative to the lower part 20 in the flexion direction, the rotationally rigid coupling of the pivot piston 30 to the upper part 10 has the effect that the pivot piston 33 is pivoted counterclockwise inside the chamber 32. Hydraulic fluid, which is located in the chamber 32, is moved from the flexion chamber through the channel 36 in the housing 30, and through a throttle device 37, into the extension chamber 35. The throttle 37 can be designed to be adjustable or settable. Adjustability can be effected by a computer control on the basis of sensors. Alternatively, the throttle 37 can be set permanently to the respective user. For the adjustment, the throttle 37 can be adjusted manually and permanently from the outside via an access.

A support 41 in the form of an S-shaped rod is mounted directly at the pivot piston 33. The support 41 has a coupling point 38 at the pivot piston side. The coupling point 38 is configured such that the support 41 can be pivoted about the coupling point 38. It is thereby possible that, in the event of a flexion movement, i.e. a counter-clockwise pivoting of the pivot piston 33, the support 41 can slide on the coupling point 38, if the coupling point 38 executes a partial circular movement. The bearing in the coupling point 38 can be designed to transmit compressive force and to transmit tensile force.

The other, rounded end of the support 41 is mounted in a slide piece 43, which has a depression in which the end of the support 41 directed away from the pivot piston 33 is fitted. Here too, a rotation movement is possible in the bearing point 39 on the slide piece 43, such that the pivoting movement of the support 41, which occurs in the pivoting of the pivot piston 33, can also be executed in the bearing point 39 at the slide piece side.

The slide piece 43 is guided in a bushing 50, which is screwed into the housing 30. A helical spring 42 is arranged inside the bushing 50, such that the combination of the spring 42, the slide piece 43 and the support 41 results in a pretensioning device 40, via which compressive forces can be transmitted from a compressed spring 42 directly to the pivot piston 33.

The slide piece 43 protrudes into the chamber 32 when the pivot piston 33 is located in the position shown.

Figure 3:
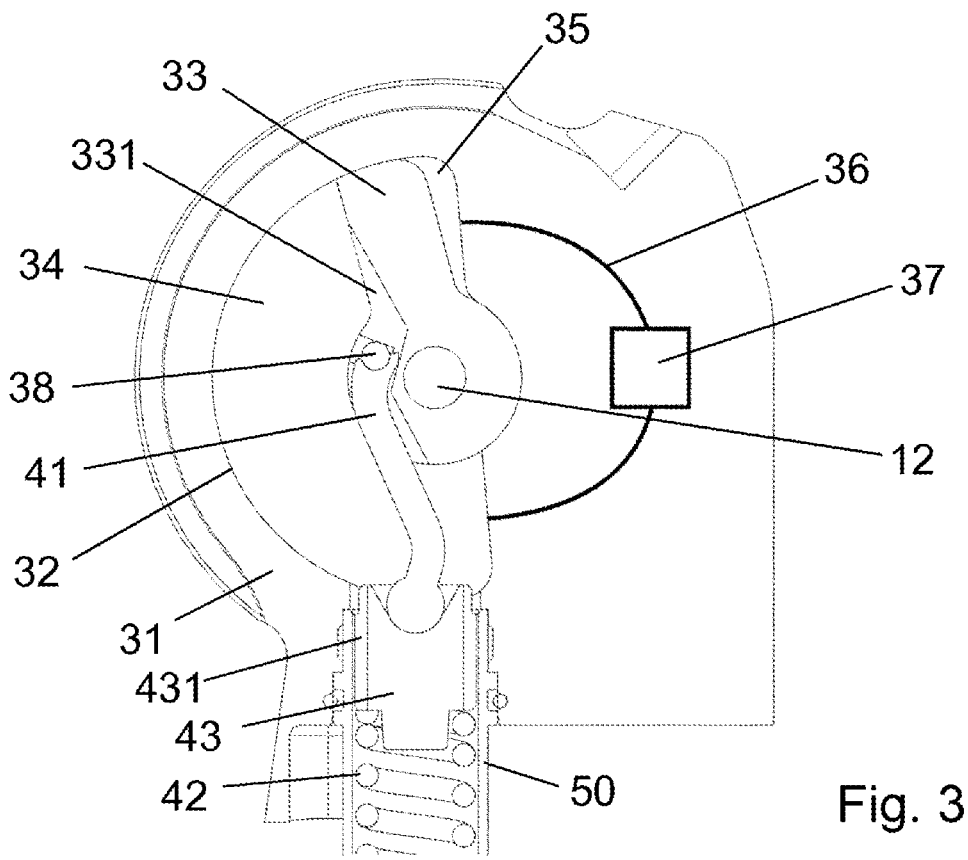
FIG. 3 shows a detailed view in the position of maximum extension.

FIG. 3 shows the position according to FIG. 2 in a partial view. Formed at the outer face of the slide piece 43 are passages, recesses or channels 431, for example in the form of grooves, through which the hydraulic liquid from the chamber 32 can flow into and out of the bushing 50. Thus, both the bushing 50 and also the chamber 32 and the connection channel 36 are filled with the hydraulic fluid. Both the spring 42 and also the slide piece 43 and the support 41 are located inside the hydraulic fluid, such that the latter at the same time assumes a lubricating function and a noise-damping function and shields the moved components of the pretensioning device 40 from external influences. The slide piece 43 is designed with the passages 431 such that the pivoting movement meets no or virtually no hydraulic resistance.

It will be seen in FIG. 3 that the pivot piston 33 has a recess 331, which is formed in the region where the support 41 is mounted at the pivot piston 33. The recess 331 can be designed as a groove and does not extend over the full width of the pivot piston 33. The recess 331 serves, among other things, to prevent a situation where, in a position of maximum flexion, the support 41 collides with the chamber inner wall 32, and therefore the greatest possible pivoting angle can be achieved. The groove-like recess 331 does not extend over the full height of the pivot piston 33 and is preferably only so wide that the support 41 can move therein. The recess 331 serves to ensure that, despite the eccentric arrangement of the bearing point 38 at the piston, the support 31 can approach as close as possible to the pivot axis 12, as a result of which a compact installation space can be achieved. The recess 331, spaced apart from the tip of the pivot piston 33 facing toward the chamber wall 32, extends as far as the opposite foot region on the side of the pivot piston 33 facing away from the pivot axis 12.

If the pivot piston 33 is rotated counter-clockwise, when the upper part 10 is flexed, the coupling point 38 of the support 41 to the pivot piston 33 migrates on a circular path about the pivot axis 12. In doing so, the coupling point 38, and with it also the support 41, is pivoted counter-clockwise about the lower bearing point 39 until the maximum lateral deflection is reached. Upon a further counter-clockwise rotation, the coupling point 38 pivots under the pivot axis, wherein, by the circular movement of the coupling point 38, the support 41, designed as a component transmitting compressive force and made of metal or of a dimensionally stable plastic, also executes a downward movement, such that the slide piece 43 is pushed into the bushing 50 counter to the spring force of the spring 42. The slide piece 43 is pushed to the maximum extent into the bushing 50 when the coupling point 38 lies perpendicularly below the pivot axis 12.

Figure 4:
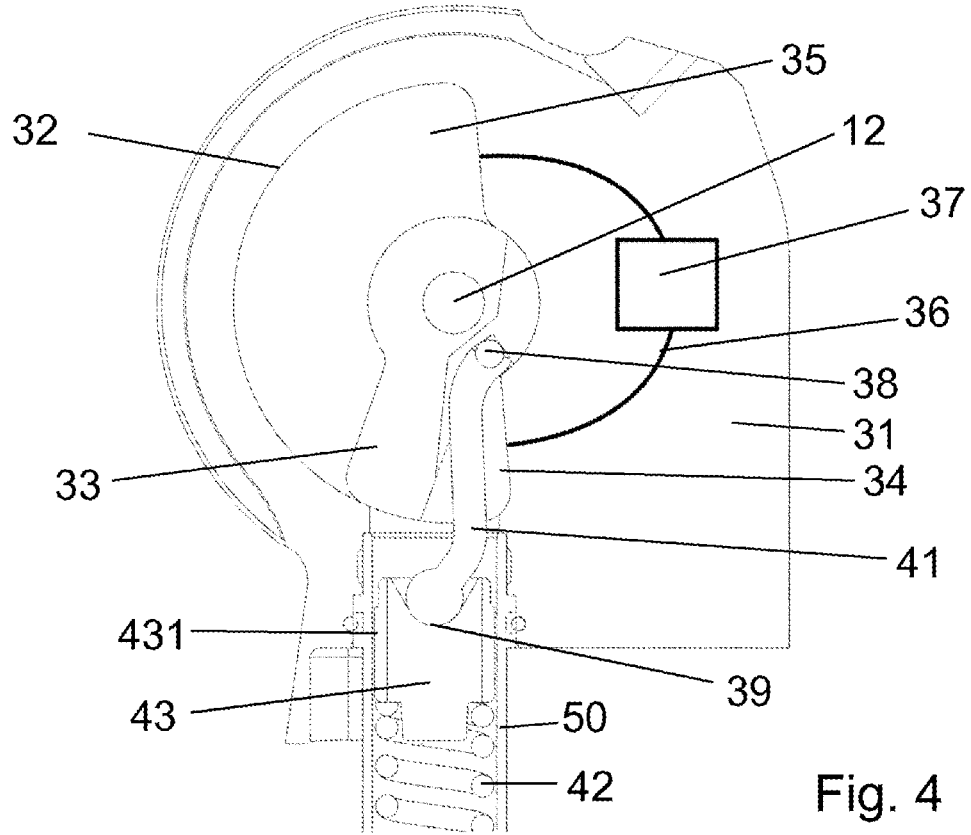
FIG. 4 shows a view of FIG. 3 in the position of maximum flexion.
Figure 5:
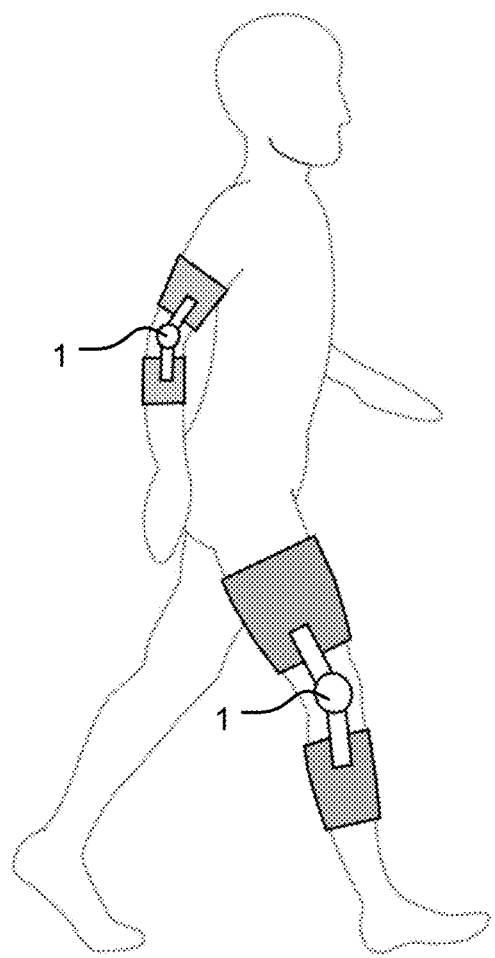
FIG. 5 shows an artificial joint incorporated into an orthosis.

FIG. 4 shows the position of almost maximum flexion of the knee joint 1, in which position the extension chamber 35 has an almost maximum volume, whereas the flexion chamber 34 has an almost minimum volume. The coupling point 38 is located to the right-hand side of the pivot axis 12, i.e. on the opposite side of the pivot axis 12 compared to the position of maximum extension according to FIG. 3. On account of the S-shaped contour of the support 41 and the recess 331 in the pivot piston 33, it is possible that the pivot piston 33 is pivotable by almost 180 degrees about the pivot axis 12. The spring 42 is located in a pretensioned state. On account of the position to the right of the pivot axis 12, the spring 42 presses the piston 43 further to the flexion position via the slide piece 43 and the support 41, since the force action line assists a corresponding rotation of the pivot piston 33 in the counter-clockwise direction. If the joint 1 is extended again, an extension assistance takes place only after the coupling point 38 has been moved to the other side of the perpendicular that runs through the rotation axis 12. The compressive force of the support 41 mounted directly at the pivot piston 33, which compressive force results from the relaxation of the spring 42, provides extension assistance and, in the case of a prosthetic knee joint, an extension movement of the lower part 20.

It is also possible in principle for such a joint device or such a joint 1 to be installed in an orthosis. Use at other joint locations is also possible, for example at an elbow joint. Instead of extension assistance, it is also possible for flexion assistance to be provided by a corresponding arrangement of the pretensioning device 40, depending on the orientation of the spring 42 and the articulation of the support 41.

On account of the constant pretensioning effected by the spring 42, the bearing of the support 41 at the upper coupling point 38 and at the lower bearing point 39 does not have to transmit tensile force. It is also possible in principle that the support 41 is mounted pivotably at the rotation piston 33, for example by a floating axle, to transmit tensile force and to transmit compressive force. The same applies for the bearing on the slide piece 43.

In addition to a rectilinear design of the bushing 50, the latter can also have a curved shape. Instead of a helical spring 42, different spring devices or force storage devices can be provided, for example disk springs, helical disk springs or the like. The bushing 50 is located inside the lower part 20. The bushing 50 can be screwed into the housing so as to permit straightforward assembly of the whole pretensioning device 40. It is thereby possible to use different springs 42 or to retrofit a corresponding joint device with a pretensioning device 40. Without a pretensioning device 40, the access to the chamber 32 is easily closed by a stopper.

We claim:

1. An orthopedic joint, comprising:
an upper part;
a lower part mounted on the upper part so as to pivot about a pivot axis;
a rotation hydraulics unit, comprising:
a housing with a chamber;
a pivot piston which is mounted pivotably in the chamber and divides the chamber into a flexion chamber and an extension chamber, the flexion and extension chambers being connected hydraulically to each other via at least one channel;
a pretensioning device which assists a pivoting movement of the upper part relative to the lower part, the pretensioning device comprising a support and a slide piece, wherein the support is coupled directly to the pivot piston at a coupling point and to the slide piece at a lower bearing point, wherein the support is positioned in a hydraulic fluid.

2. The joint as claimed in claim 1, wherein the support is mounted pivotably in or at the pivot piston.

3. The joint as claimed in claim 1, wherein the support is stable against buckling of the support.

4. The joint as claimed in claim 1, wherein the support transmits at least one of tensile force and compressive force from the slide piece to the pivot piston.

5. The joint as claimed in claim 1, wherein the pretensioning device has a spring, on or at which the support is mounted.

6. The joint as claimed in claim 5, wherein the support is mounted on or at the slide piece, which is arranged between the spring and the support.

7. The joint as claimed in claim 6, wherein the slide piece is guided in a bushing, which is connected fluidically to the chamber.

8. The joint as claimed in claim 6, further comprising at least one of a recess and a passage for a hydraulic fluid arranged in or at the slide piece.

9. The joint as claimed in claim 1, further comprising a recess, in which the support is received, formed in the pivot piston.

10. The joint as claimed in claim 1, wherein the support has an S-shaped contour.

11. The joint as claimed in claim 1, wherein the coupling point is positioned on a first side of the pivot axis when the joint is in a position of maximum extension and the coupling point is positioned on a second side of the pivot axis when the joint is in a position of maximum flexion, the first side opposite the second side.

12. The joint as claimed in claim 1, wherein the channel is formed in the housing.

13. The joint as claimed in claim 1, wherein a throttle is arranged in the channel.

14. The joint as claimed in claim 1, wherein the joint is suitable for a prosthesis or orthosis and is designed as a prosthetic joint or an orthotic joint.

15. An orthopedic joint, comprising:
an upper part;
a lower part pivotally mounted on the upper part about a pivot axis;
a rotation hydraulics unit, comprising:
a housing having a chamber;
a pivot piston mounted pivotably in the chamber to divide the chamber into a flexion chamber and an extension chamber, the flexion and extension chambers being connected hydraulically via at least one channel;
a pretensioning device connecting the flexion and extension chambers, operable to assist a pivoting movement of the upper part relative to the lower part, the pretensioning device comprising a support and a slide piece, wherein the support is coupled directly to the pivot piston at a coupling point and to the slide piece at a lower bearing point, wherein the support is positioned in a hydraulic fluid.

16. The joint as claimed in claim 15, wherein the support is mounted pivotably in or at the pivot piston.

17. The joint as claimed in claim 15, wherein the support is stable against buckling of the support.

18. The joint as claimed in claim 15, wherein the support transmits at least one of tensile force and compressive force from the slide piece to the pivot piston.

* * * * *